US00PP32248P2

(12) United States Plant Patent
Hansen

(10) Patent No.: US PP32,248 P2
(45) Date of Patent: Sep. 29, 2020

(54) ***PHLOX* PLANT NAMED 'ROCKY ROAD GRAPE'**

(50) Latin Name: ***Phlox* hybrid**
Varietal Denomination: Rocky Road Grape

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,085

(22) Filed: Jan. 30, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden

(57) ABSTRACT

A unique cultivar of Hybrid Creeping *Phlox* named 'Rocky Road Grape' characterized by vigorous, dense, spreading, multi-stemmed, winter-hardy habit with short, bright glossy-green, linear leaves. Flowering begins in mid-April and continuing for up to five weeks, in cool conditions, on heavily-branched peduncles and completely cover the plant in peak season. Petals are red-purple with a small dark-purple eye. Petals lighten to soft lavender with maturity. Petal apices are deeply notched. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Rocky Road Grape'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 1, 2019. Subsequently, the new plant was advertised in the "Walters Gardens 19-20 Catalog" by Walters Gardens, Inc. released on May 29, 2019. The claimed plant was first sold on Jul. 8, 2019 by Walters Gardens, Inc., who obtained the plant and all information relating thereto, from the inventor. No plants of *Phlox* 'Rocky Road Grape' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant, known as *Phlox* 'Rocky Road Grape' and will be referred to hereafter by its cultivar name, 'Rocky Road Grape', or the "new plant". The new plant was hybridized by the inventor at a wholesale perennial nursery in Zeeland, Mich. on Mar. 24, 2015 as cross between a proprietary selection of *Phlox bifida* subsp. *stellaria* (not patented) as the female parent times *Phlox douglasii* 'Crackerjack' (not patented) as the male parent. The new plant passed initial evaluation on the spring of 2017 and was assigned the breeder code 15-141-7 through the remaining evaluation process. 'Rocky Road Grape' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Rocky Road Grape' is unique from all other Hybrid Creeping *Phlox* known to the inventor. The nearest comparison plants known to the inventor include: the female and male parents, 'Red Wing' (not patented), 'Lemhi Purple' (not patented), 'Rocky Road Pink' U.S. Plant Pat. No. 31,486, 'Rocky Road Magenta' U.S. Plant Pat. No. 31,485, 'Rocky Road Periwinkle' copending U.S. Plant patent application Ser. No. 16/873,084, 'Rocky Road Violet Blue' copending U.S. Plant patent application Ser. No. 16/873,083 and 'Plumtastic' U.S. Plant Pat. No. 28,896. The proprietary selection of *Phlox bifida* subsp. *stellaria* has flowers that have narrow flower petals of soft blue coloration and less flower coverage of the plant when in peak bloom. 'Crackerjack' has flowers that are more open with narrower petals, light magenta-red with less deeply cleft petal lobe apices. 'Red Wing' has flowers of bright crimson-pink with more vigorous growth and spreading. 'Lemhi Purple' has more purple flowers without a notched petal apex. 'Rocky Road Pink' has pastel rosy-pink flowers with a dark pink eye. 'Rocky Road Magenta' has magenta purple flowers without a notched petal apex and the flowers are much larger. 'Rocky Road Periwinkle' has flowers that are periwinkle-blue flowers without notches on the petal apices, and the flower color does not change significantly with maturity. 'Rocky Road Violet Blue' has flowers of violet-blue coloration and small apical notches on the petals and the color does not lighten significantly with maturity. 'Plumtastic' has flowers of violet-pink with purple markings near the eye, and the flower initially has a light, near-white center that darkens to the same violet-pink at maturity.

*Phlox* 'Rocky Road Grape' differs from and all other *Phlox* known to the inventor in the following repeatedly observed traits in combination:

1. Vigorous plants of dense spreading habit, spreading by rooting stems, producing short, clean, puberulent, bright-green, linear leaves;
2. Multiple heavily-branched stems produce branched panicles;
3. Flower beginning in mid-April and continuing for up to five weeks in cool weather, completely covering plant at peak flowering;
4. Flowers of red-purple, lightens to soft lavender with maturity, with deep notches at the tip of the petals;
5. Plant is able to withstand dry conditions once established.

BRIEF DESCRIPTION OF THE DRAWINGS

The photographs of the new plant demonstrate the unique traits of *Phlox* 'Rocky Road Grape' and the overall appearance of the plant at three-years-old growing in a full-sun trial beds in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
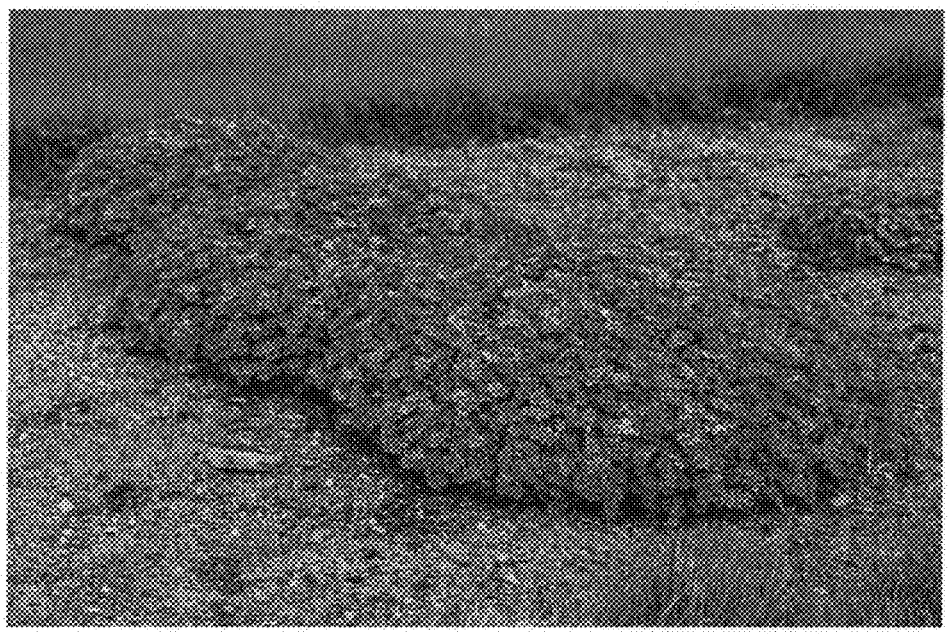
FIG. 1 shows a habit view of the new plant in peak flower.
Figure 2:
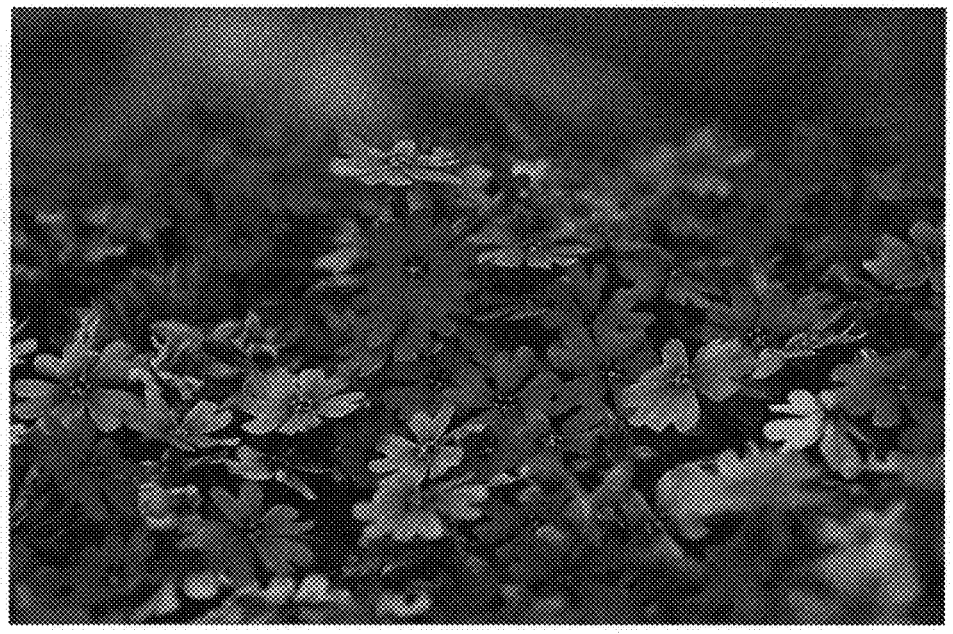
FIG. 2 shows a close-up of the flowers and buds.

The following descriptions and color references are based on the 2015 edition of The Royal Horticultural Society Colour Chart except where common dictionary terms are used. *Phlox* 'Rocky Road Grape' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is a proprietary selection of *Phlox bifida* subsp. *stellaria*, male or pollen parent is *Phlox douglasii* 'Crackerjack';

Plant habit: Winter-hardy, evergreen herbaceous perennial; short, dense, producing about 80 to 100 stiff, highly-branched prostrate stems; foliage 8.0 cm tall and 60.0 cm wide, average 7.5 cm tall and 45.0 cm wide; flowering to 10.0 cm tall and 62.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear to subulate; apex narrowly acute to apiculate; base truncate, clasping; margin entire, ciliolate; puberulent both adaxial and abaxial; about 15.0 mm long by about 3.5 mm wide, average about 12.5 mm long and 2.5 mm wide;

Leaf color: Adaxial expanding and mature nearest RHS 137A; abaxial expanding and mature nearest RHS 146B;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; prostrate; highly branching; to about 7.0 mm long and 1.0 mm diameter near base;

Stem color: Color nearest RHS 145A when exposed;

Nodes: Proximally about 5.0 mm apart; distally less than 1.0 mm apart;

Node color: Color nearest RHS 183D;

Inflorescence: Upright to outwardly; about 2.5 cm long and 4.0 cm wide; average of 4 flowers;

Flowers: Perfect; salverform; mostly flat faced; about 21.0 mm across face and 14.0 mm long; with fused corolla tube about 12.0 mm long and 2.0 mm diameter near face; attitude upright to outwardly;

Flower longevity: About 5 days on plant; self-cleaning;

Flower fragrance: Not detected;

Buds one to two days prior to opening: Narrowly oblanceolate, to narrowly clavate; bluntly acute apex with rounded base; petals implicate; about 16.0 mm long, 5.0 mm long in terminal bulb portion and 7.0 mm long in tube; corolla tube to 2.0 mm diameter, bulb to 4.0 mm diameter;

Bud color: Exposed petal bulb portion deeper and darker than RHS N78A, between tube and bulb nearest RHS 79A, corolla tube basal 1.0 mm nearest RHS 145B and distal tube nearest RHS 79D; calyx nearest 138A with strong blush in high light exposure of nearest RHS N187A;

Petals: Five; consisting of limb and claw base fused into corolla tube; apex rounded and deeply cleft to about 3.0 mm deep; limbs not imbricate; margin entire; glabrous adaxial and abaxial;

Petal size: Limb about 9.5 mm long and 8.0 mm wide near middle; tube about 12.0 mm long and 2.0 mm diameter;

Petal color upon opening:

*Adaxial*.—Limb between RHS N79C and RHS N78A, with small marks near center eye of nearest RHS N92A; proximal 2.5 mm of tube nearest RHS 145B, remaining distal tube portion nearest RHS 79D.

*Abaxial*.—Limb between RHS N78A and RHS N78B, proximal 2.0 mm of tube nearest RHS 145B and remaining tube portion between RHS 79D.

Petal color upon maturity:

*Adaxial*.—Limb nearest N78A, without marks near center eye; proximal 2.5 mm of tube nearest RHS 145B, remaining distal tube portion nearest RHS 79D.

*Abaxial*.—Limb between RHS N78A and RHS N78B, proximal 2.0 mm of tube nearest RHS 145B and remaining tube portion between RHS 79D.

Androecium: Typically five;

Filaments: Typically five, adnate to inner corolla to various heights about 6.0 mm to 10.0 mm from base; free in the distal 1.0 mm to 2.0 mm long and 0.2 mm in diameter; color nearest RHS NN155D;

Anther: Five; oblong elliptic; basifixed; oblong, about 2.0 mm long by 1.0 mm wide; color nearest RHS 15A;

Pollen: Nearly microscopic; color nearest RHS 23A;

Gynoecium: One pistil per flower; 11.0 mm long;

Style: Cylindrical; about 8.5 mm long and 0.3 mm diameter when flower is mature; persistent after flower abscission; color nearest RHS 145D;

Stigma: Trifid in proximal 1.0 mm long, about 0.3 mm diameter; color nearest RHS 12A;

Ovary: Inferior; conical; glabrous; acute apex and truncate base; about 1.5 mm long and 1.0 mm diameter; color nearest RHS 144A;

Calyx: Campanulate; pubescent abaxial, glabrous adaxial; about 7.0 mm long and 3.0 mm across at apex;

Sepals: Five; lanceolate; glabrous adaxial and pubescent to puberulent abaxial; narrowly acute apex, fused in basal 4.0 mm; margin entire; matte abaxial, and lustrous adaxial; individually about 8.0 mm long and 1.0 mm wide at fusion;

Sepal color: Adaxial nearest RHS 137A in dorsal region and RHS 138A in ventral region; abaxial nearest RHS 138A and strong blush with high light exposure nearest RHS N187A;

Peduncle: Finely puberulent; strong, flexible; mostly upright; cylindrical; about 1.5 mm diameter at base and 1.5 cm long;

Peduncle color: Low light or ventrally nearest RHS 146D; high light or ventrally nearest RHS 146C with strong blush to solid RHS 187A;

Pedicle: Cylindrical; finely puberulent; flexible; upright to outwardly; variable lengths from about 5.0 mm to 16.0 mm long and 0.7 mm diameter;

Pedicle color: Variable depending on light exposure; low light or ventrally nearest RHS 146D; high light or dorsally nearest RHS 146C with strong blush to solid RHS 187A;

Fruit and seeds: Not observed;

Hardiness and culture: The new plant grows best with full sun, light moisture and deep drainage; hardy to at least from USDA zone 4 through 8.

Disease and pest resistance: *Phlox* 'Rocky Road Grape' demonstrates excellent powdery mildew resistance under conditions that would normally show symptoms.

I claim:

1. A new and distinct cultivar of Hybrid Creeping *Phlox, Phlox* plant named 'Rocky Road Grape' as herein described and illustrated.

* * * * *